US008741487B1

(12) United States Patent
Duggan et al.

(10) Patent No.: US 8,741,487 B1
(45) Date of Patent: Jun. 3, 2014

(54) ELECTRODE CURRENT COLLECTOR WITH STRESS-RELIEVING MESH STRUCTURE

(75) Inventors: John C. Duggan, Tonawanda, NY (US); Michael R. Blendowski, Williamsville, NY (US); Donald F. Kaiser, Clarence Center, NY (US); Ashish Shah, East Amherst, NY (US)

(73) Assignee: Greatbatch Ltd., Clarence, NY (US)

( * ) Notice: Subject to any disclaimer, the term of this patent is extended or adjusted under 35 U.S.C. 154(b) by 864 days.

(21) Appl. No.: 12/549,435

(22) Filed: Aug. 28, 2009

Related U.S. Application Data (60) Provisional application No. 61/092,498, filed on Aug. 28, 2008.

(51) Int. Cl.
| | |
|---|---|
| H01M 4/72 | (2006.01) |
| H01M 4/74 | (2006.01) |
| B23P 13/00 | (2006.01) |
| H01M 4/76 | (2006.01) |
| B21D 31/04 | (2006.01) |

(52) U.S. Cl.
USPC ............... 429/242; 429/233; 429/241; 29/2; 29/6.1

(58) Field of Classification Search
USPC .................. 429/233–245; 29/2, 6.1
See application file for complete search history.

(56) References Cited

U.S. PATENT DOCUMENTS

| | | | |
|---|---|---|---|
| 1,044,831 A | 11/1912 | Wackwitz | |
| 1,528,963 A | 3/1925 | Adams et al. | |
| 2,503,970 A | 4/1950 | Rupp | |
| 3,532,545 A | 10/1970 | Babusci et al. | |
| 3,907,593 A * | 9/1975 | Marincic | 429/345 |
| 4,118,553 A | 10/1978 | Buckethal et al. | |
| 4,151,331 A * | 4/1979 | Hug et al. | 429/94 |
| 4,221,852 A | 9/1980 | Qureshi | |
| 4,251,603 A | 2/1981 | Matsumoto et al. | |
| 4,283,844 A * | 8/1981 | Milden et al. | 29/623.5 |
| 4,291,443 A * | 9/1981 | Laurie et al. | 29/6.1 |
| 4,315,060 A * | 2/1982 | Goebel et al. | 429/122 |
| 4,320,183 A | 3/1982 | Qureshi | |
| 4,477,546 A | 10/1984 | Wheeler et al. | |
| 4,528,255 A | 7/1985 | Hayes et al. | |
| 4,994,334 A | 2/1991 | Ikoma et al. | |
| 5,093,971 A * | 3/1992 | Hein | 29/6.1 |
| 5,415,949 A | 5/1995 | Stone et al. | |
| 5,434,019 A | 7/1995 | Zhang et al. | |
| 5,582,936 A | 12/1996 | Mrotek et al. | |
| 5,989,749 A | 11/1999 | Kao et al. | |
| 6,037,081 A | 3/2000 | Kashio et al. | |
| 6,203,948 B1 | 3/2001 | Kao et al. | |
| 6,210,826 B1 | 4/2001 | Dopp et al. | |

(Continued)

*Primary Examiner* — Sonya Mazumdar
(74) *Attorney, Agent, or Firm* — Michael F. Scalise (57) ABSTRACT

A current collector comprising a frame conductor formed as a closed undulating perimeter, and a conductive mesh formed within the frame conductor is described. The conductive mesh is comprised of a plurality of radial struts, each radial strut having a central end and an outer end. The radial struts emanate from a junction within the undulating perimeter with their outer ends connected to the undulating perimeter of the frame. The conductive mesh may include branch struts having proximal ends and distal ends, with the proximal ends connected to the radial struts. The distal ends of the branch struts may be connected to the undulating perimeter, or to adjacent radial struts. The current collector is used in an electrochemical cell, wherein a first electrode active material is contacted to at least one of first and second major sides of the current collector to provide a first electrode.

30 Claims, 5 Drawing Sheets

(56) References Cited

U.S. PATENT DOCUMENTS

| | | | |
|---|---|---|---|
| 6,212,744 B1 * | 4/2001 | Inanobe et al. | 29/6.1 |
| 6,245,462 B1 | 6/2001 | Kao et al. | |
| 6,274,274 B1 | 8/2001 | Schaeffer et al. | |
| 6,447,957 B1 * | 9/2002 | Sakamoto et al. | 429/242 |
| 6,893,777 B2 | 5/2005 | Probst | |
| 6,921,611 B2 | 7/2005 | Schaeffer et al. | |
| 6,953,641 B2 | 10/2005 | Chen | |
| 7,000,297 B2 | 2/2006 | Frustaci et al. | |
| 7,056,620 B2 | 6/2006 | Krasnov et al. | |
| 7,814,628 B2 * | 10/2010 | Fujiwara et al. | 29/6.1 |
| 7,976,976 B2 * | 7/2011 | Tomantschger | 429/135 |
| 8,142,935 B2 * | 3/2012 | Fujiwara et al. | 429/242 |
| 2003/0082455 A1 * | 5/2003 | Fujiwara et al. | 429/242 |
| 2003/0129479 A1 * | 7/2003 | Munenaga et al. | 429/94 |
| 2004/0005498 A1 * | 1/2004 | Eshraghi | 429/140 |
| 2005/0164091 A1 | 7/2005 | Schaeffer et al. | |
| 2007/0193009 A1 * | 8/2007 | Vincze et al. | 29/2 |

\* cited by examiner

ELECTRODE CURRENT COLLECTOR WITH STRESS-RELIEVING MESH STRUCTURE

CROSS-REFERENCE TO RELATED APPLICATION

This application claims priority from U.S. Provisional Application Ser. No. 61/092,498, filed Aug. 28, 2008.

BACKGROUND OF THE INVENTION

1. Field of the Invention

The present invention relates generally to current collectors used in electrodes of electrochemical cells. More particularly, the present invention relates in one embodiment to a current collector that can deform compliantly during electrode manufacturing and cell operation, thereby avoiding electrode deformation and delamination.

2. Description of Related Art

Compact electrochemical cells or batteries, such as those used to power implantable medical devices, are comprised of an anode and cathode contained within a casing and activated by an electrolyte. Either or both electrodes may include respective electrode active materials that are contacted with opposed first and second sides of a conductive current collector. The current collector is typically formed of a metal screen. Depending upon the cell configuration, the current collector may be connected directly to the casing or, to a terminal wire that exits through and is insulated from the cell casing.

From the beginning of the manufacturing process when electrode active material is contacted to a current collector to form an electrode to the end of cell life, stresses may arise in the electrode. These stresses tend to deform the electrode and cause delamination of the electrode active material from the current collector. Both effects are undesirable and can degrade performance and life of the cell.

Thus, a need exists for a battery current collector that has a more physically compliant structure, which can serve to relieve stresses that would otherwise occur in a non-compliant current collector screen. This need has become more evident in certain cathode structures comprised of materials that change shape, i.e., expand, 'relax', etc., during and after the electrode farthing process. Such cathodic structures, when formed, essentially become a composite matrix having a current collector or collectors in combination with one or more types of cathode base materials typically structured in layers. The initial physical form of such cathodic materials before assembly can be sheet, powder, granular, etc.; when formed they essentially become a solid.

Typical prior art current collectors are comprised of a metal screen having a regular pattern of repeating geometric openings or perforations. The shape of such openings may be that of a diamond, square, circle, hexagon, etc. As such, the current collector is essentially the network-like structure remaining after the pattern of openings has been established. Various methods are used to manufacture typical current collectors, such as "punching-stretching" for expanded metal, punching for perforated plate, fine blanking, chemical etching, weaving (such as in wire cloth manufacture), laser cutting, and electroforming.

In addition to their primary function of providing conductivity from the active material to the associated terminal for the cell circuit, current collectors may serve as structural reinforcement in electrodes, particularly cathodes. However, in some cell chemistries, combinations of certain cathode materials formed in a composite matrix contacted to a current collector of the typical, prior art kind have been problematic. In such cathodic structures, conventional current collectors are not able to move sufficiently with the expansion of the cathodic base materials during and after the manufacturing process. The resultant problem manifests itself via a physically constraining effect produced by the one or more embedded current collectors. Thus, stresses develop between the cathode active material and the current collector.

Such stresses may be analogous to the condition present in bimetallic springs used to produce movement of a mechanism. Bimetallic springs are a composite structure formed of at least two components having different coefficients of thermal expansion. Such stresses work as intended in bimetallic springs, since the components remain sufficiently flexible throughout a given temperature range and have a relatively high tensile strength. However, when a similar expansion occurs within certain cathode assemblies, the self-induced stresses can significantly distort or even fracture the cathode assembly, causing delamination of the cathode active materials from the current collector. For such cathode structures that are problematic, the expansion rates of the active material and the current collector are significantly different during and after the assembly process. In the case of fracture, the relatively low tensile strength of the cathode active material is a factor. Hence, there remains a need for a cathode current collector that is more compliant during and following the cathode assembly process than is presently available.

SUMMARY OF THE INVENTION

The problems of stress-induced deformation and delamination in an electrochemical cell electrode are solved by providing a current collector having a high degree of compliance. The present current collector is comprised of a frame conductor formed as a closed undulating perimeter, and a conductive mesh formed within the frame conductor. The conductive mesh is comprised of a plurality of radial struts, each having a central end and an outer end. The outer ends of the radial struts are connected to the undulating perimeter of the frame conductor. The radial struts emanate from a junction within the undulating perimeter. The current collector is typically made of a conductive metal such as aluminum, stainless steel, titanium, etc., but can be of any electrically conductive material. The current collectors disclosed herein may be used for cathodic and anodic structures.

The junction may be located in a central region of the conductive mesh, or it may be located near the undulating perimeter. The junction may be contiguous with a portion of the frame conductor of the mesh. The conductive mesh may further include the junction being formed as a node cluster comprised of a border surrounding an opening. The central ends of the radial struts are connected to the node cluster.

The undulating perimeter is comprised of convex regions and concave regions, with nodes in which the perimeter curvature transitions from concave to convex. The outer ends of the radial struts are preferably connected to the undulating perimeter at the convex regions or the nodes. The radial struts may be linear or curvilinear.

The conductive mesh may be further comprised of branch struts having proximal ends and distal ends, with the proximal ends connected to the radial struts. The distal ends of the branch struts may be connected to the undulating perimeter, preferably to the convex regions or the nodes, or to other adjacent radial struts. The branch struts may depart from the radial struts at an acute angle, such that the mesh has the appearance of the major veins of a dicot leaf. Alternatively, the branch struts may bridge the gaps between adjacent radial struts at a substantially perpendicular angle, such that the mesh has the appearance of a spider web. The branch struts may be linear or curvilinear.

The above current collectors may be used in an electrochemical cell, wherein a first electrode active material is contacted to at least one of a first and a second major sides thereof having its frame conductor connected to a first terminal to provide a first electrode. The current collector preferably includes a tab extending from the frame conductor for connection to the first terminal. A second, counter electrode electrically associated with the first electrode is connected to a second terminal housed inside of a casing. An electrolyte is delivered into the casing to activate the first and second electrodes.

The foregoing and additional objects, advantages, and characterizing features of the present invention will become increasingly more apparent upon a reading of the following detailed description together with the included drawings.

BRIEF DESCRIPTION OF THE DRAWINGS

The present invention will be described by reference to the following drawings, in which like numerals refer to like elements, and in which.

The present invention will be described in connection with a preferred embodiment, however, it should be understood that there is no intent to limit the invention to the embodiment described. On the contrary, the intent is to cover all alternatives, modifications, and equivalents as may be included within the scope of the invention as defined by the appended claims.

DETAILED DESCRIPTION OF THE PREFERRED EMBODIMENTS

In the present invention, the term "node" refers to the intersection of linear or curvilinear portions of the current collector. For example, a node is thus formed by the intersection of two or more of the following: branch strut, radial strut, terminal strut, concave portion of a frame conductor, convex portion of a frame conductor, terminal tab.

The term "undulating perimeter" refers to the outer conductive portion of the current collector having a generally sinusoidal shape of alternating convex and concave portions. From a perspective interior of the undulating perimeter and looking at the outer perimeter strand, a "convex" portion thereof or, a "convexity", is a portion of the perimeter having its trough extending inwardly and a "concave" portion or, a "concavity", is a portion of the perimeter having its trough extending outwardly.

Figure 1:
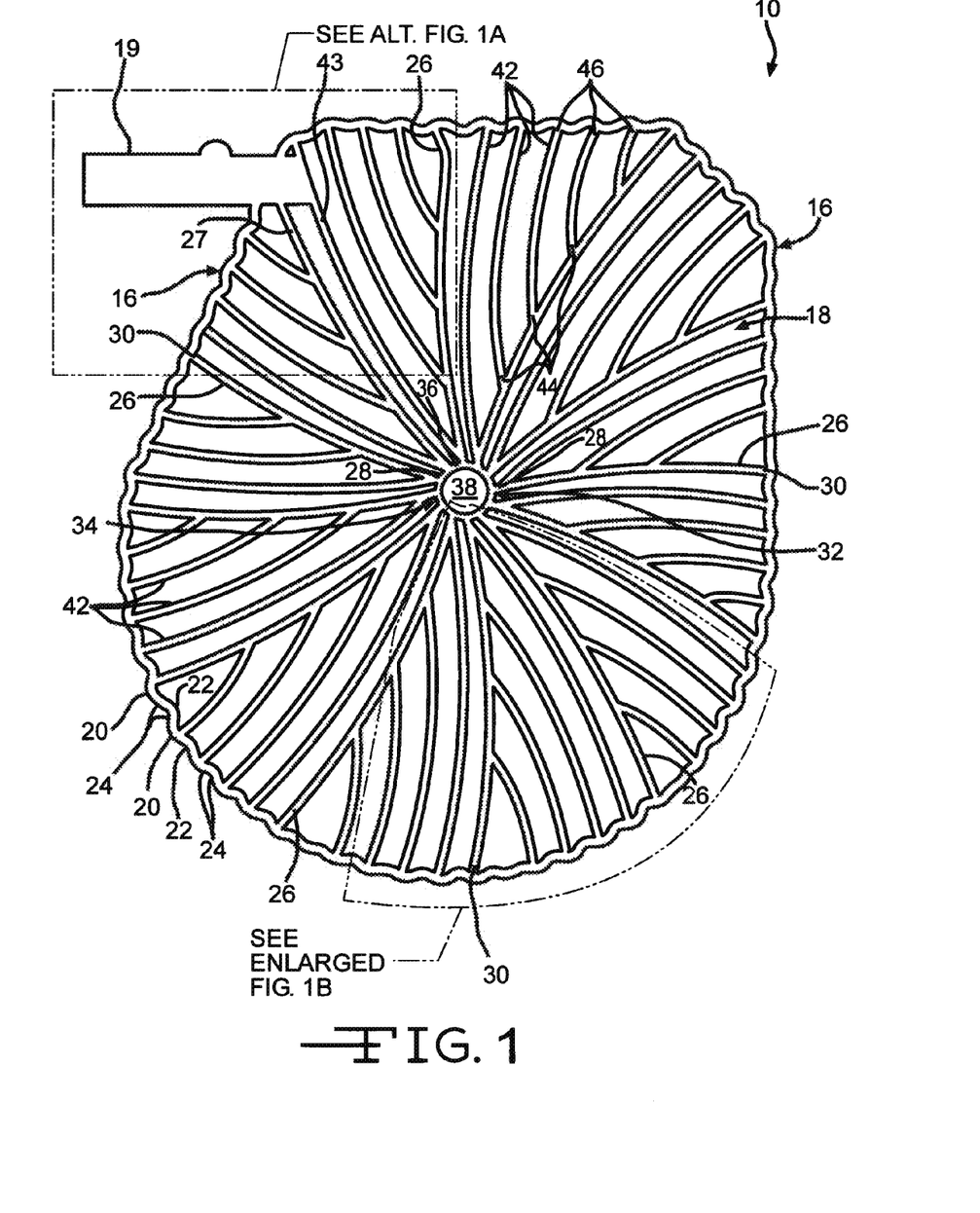
FIG. 1 is a plan view of a first current collector 10 in accordance with the present invention.
Figure 2:
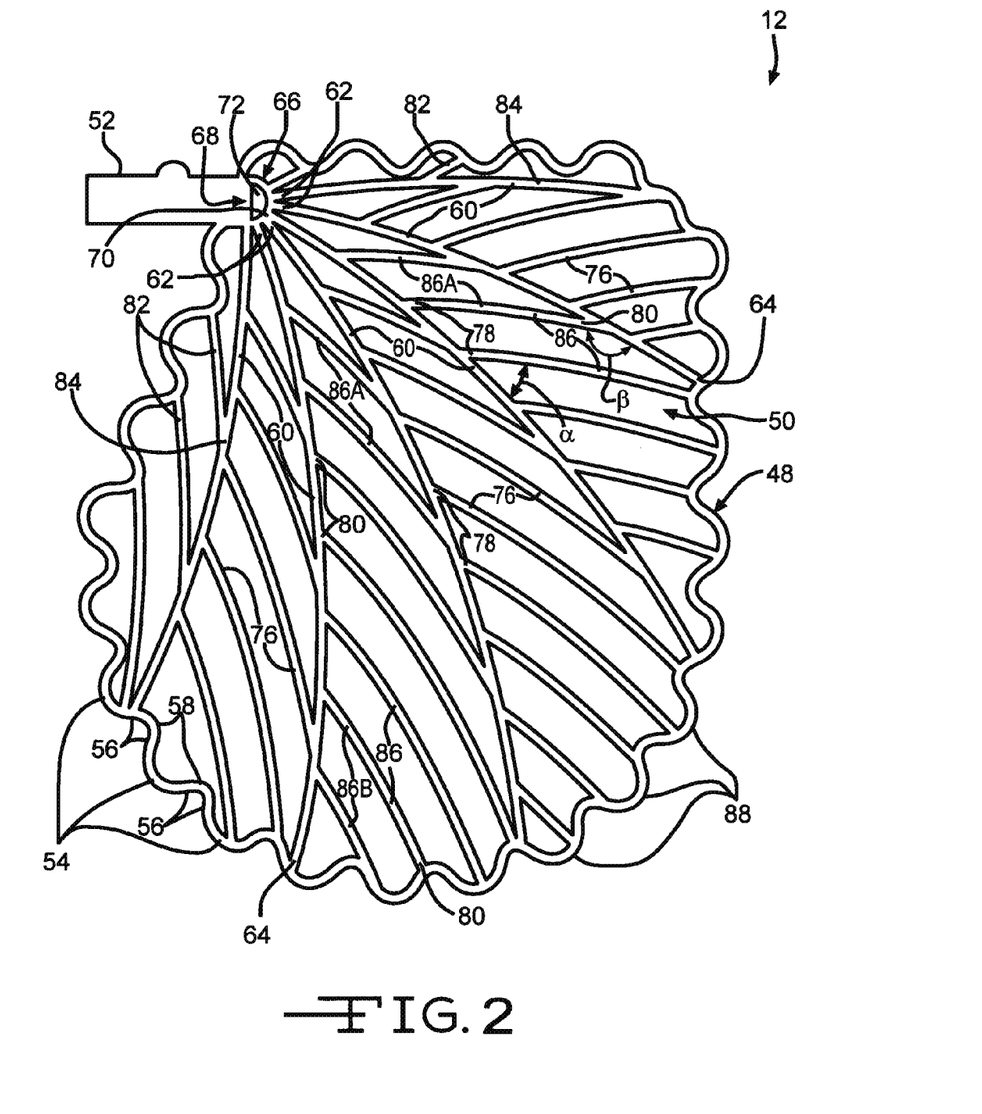
FIG. 2 is a plan view of a second current collector 12 in accordance with the present invention.
Figure 3:
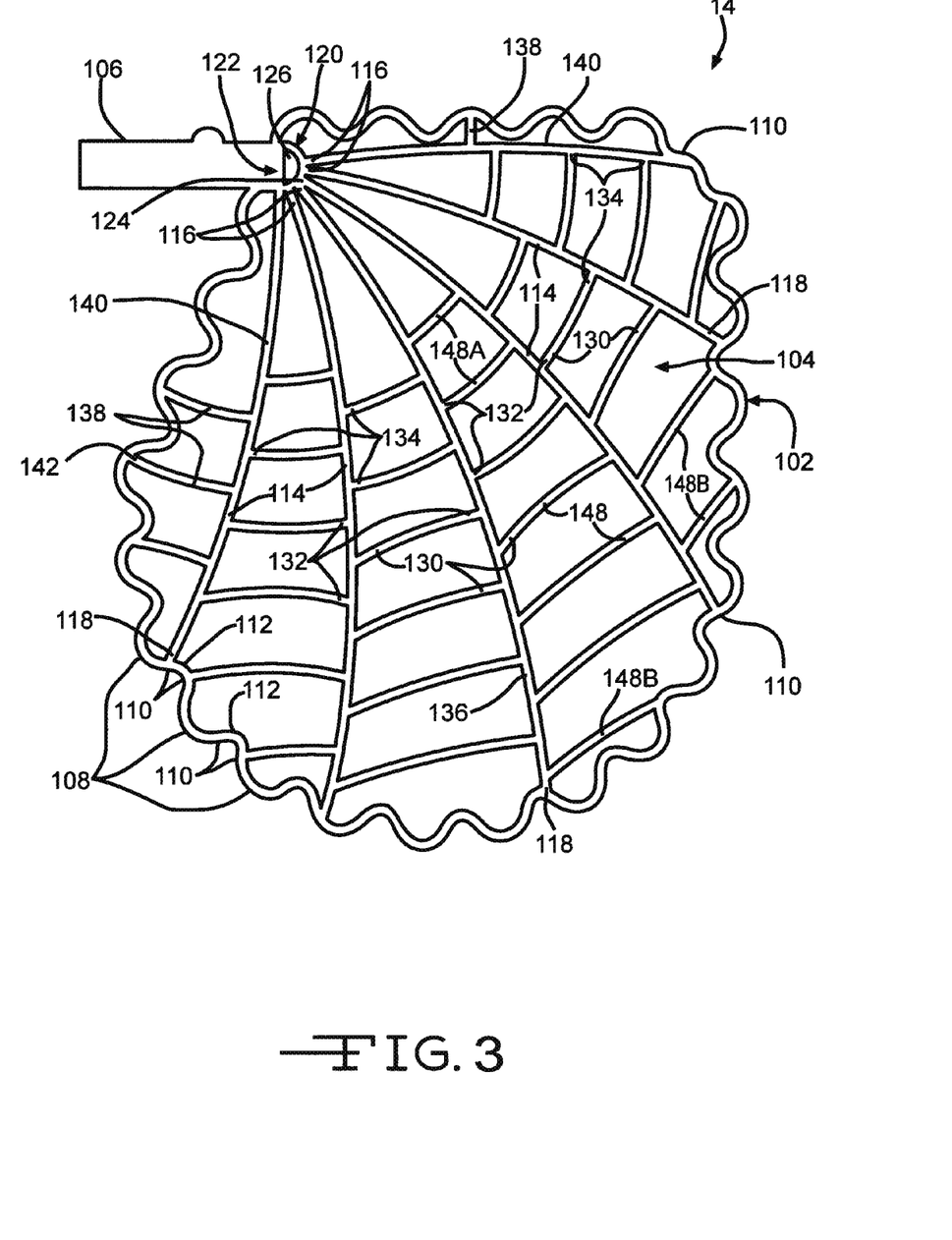
FIG. 3 is a plan view of a third current collector 14 in accordance with the present invention.

FIGS. 1 to 3 depict respective first, second, and third current collectors in accordance with the present invention. The current collectors 10, 12 and 14 share a number of common features. All are comprised of a frame formed as a closed undulating perimeter and a conductive mesh formed within the frame and comprised of a plurality of radial struts. Each of the current collectors 10, 12 and 14 is further optionally comprised of a node cluster and branch struts connected to the radial struts and to the undulating perimeter or, to adjacent radial struts. These features enable the present current collectors to deform compliantly with the cathode base material. That is both immediately following contact and pressing of the active material mixture to the current collector and after the cathode is built into a cell activated with electrolyte, and during use of the cell as the cathode active material undergoes electrochemical reaction with the anode active material. In that manner, the present current collectors serve to relieve stress in the cathode assembly, thereby avoiding "cupping" (i.e. warping into a curved shape) or delamination of the active material from the current collector. The features may also provide a more optimal current pathway from the cathode terminal pin to the cathode active material.

Turning now to FIG. 1, current collector 10 is comprised of a frame conductor 16 formed as a closed undulating perimeter and a conductive mesh 18 formed within the frame 16. The current collector 10 may include a tab 19 extending from the frame conductor 16 for connection to a terminal (not shown) of an electrochemical cell. The undulating perimeter of the frame 16 is comprised of a continuous sequence of convex regions or convexities 20, and concave regions or concavities 22. The curvature of the undulating perimeter reverses from concave to convex and vice-versa at inflection nodes 24. The terms "convex," "convexities," "concave" and "concavities" when used with respect to the undulating perimeter of the frame conductor 16, are from a reference point within the frame 16. Convexities 20 are regions of outward curvature, and concavities 22 are regions of inward curvature of the frame 16.

The conductive mesh 18 is comprised of a plurality of radial or major struts 26. Each radial strut 26 has a central or proximal end 28 and an outer or distal end 30. The outer ends 30 of the radial struts 26 are connected to the undulating perimeter of the frame 16, preferably at the convexities 20 or at the inflection nodes 24. The radial struts 26 may be linear or curvilinear, emanating from a junction 32 located within the undulating perimeter. In the current collector 10 of FIG. 1, the junction 32 is located in the central region of the conductive mesh 18 with the radial struts 26 extending outwardly like wheel spokes. That is in contrast to having the junction 32 being located in contact with the undulating perimeter as in the respective current collectors 12 and 14 of FIGS. 2 and 3.

Figure 1A:
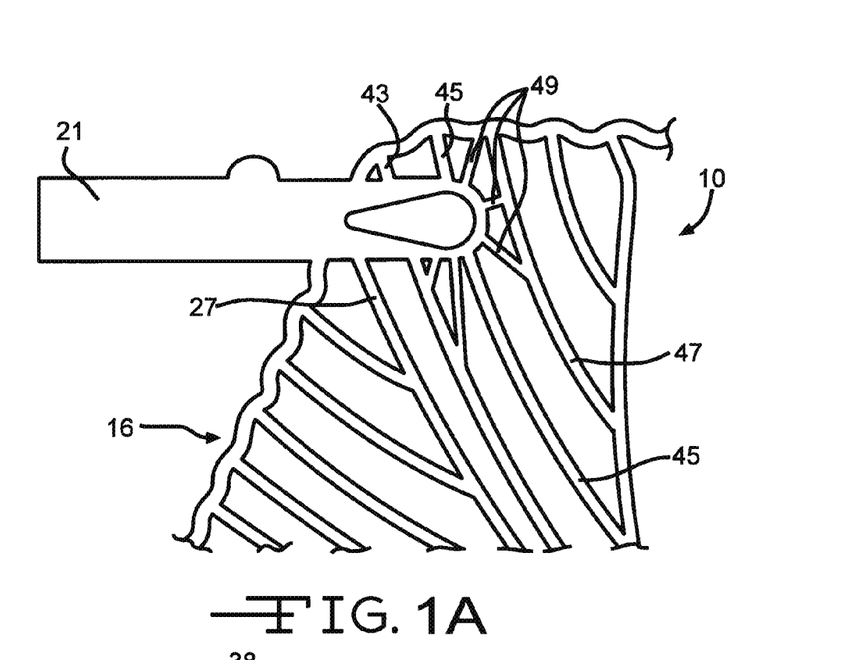
FIG. 1A is a detailed view of a connection of a terminal tab 21 that is an alternative to the tab connection depicted in FIG. 1.
Figure 1B:
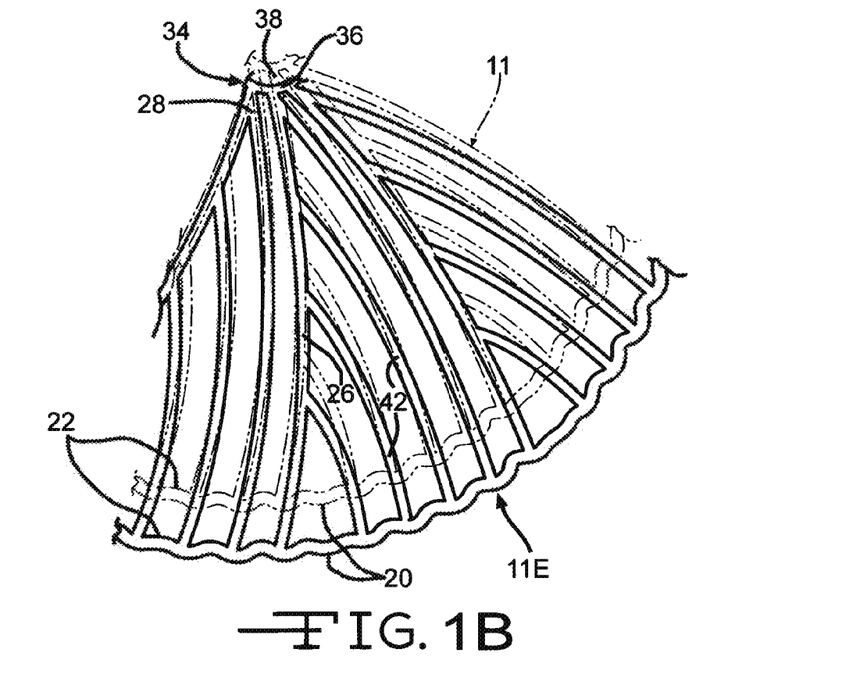
FIG. 1B is a detailed view of a sector of the current collector 10 of FIG. 1, showing compliance of the current collector.

As shown in FIG. 1B, the conductive mesh 18 may further include the junction 32 being formed as a node cluster 34 comprised of a border 36 surrounding an opening 38. The central ends 28 of the radial struts 26 are connected to the node cluster 34. The border 36 of the node cluster 34 may undulate if the opening 38 is sufficiently large, with the radial struts 26 preferably connected at concavities of the border 36 (not shown) thereof. The width of the border 36 may also be made wider than shown in FIG. 1 to provide it with additional strength. The radial struts 26 may be wider at their central ends 28, tapering to a lesser width at their outer ends 30.

The conductive mesh 18 may be further comprised of branch or minor struts 42 having proximal ends 44 and distal ends 46, with the proximal ends 44 being connected to the major or radial struts 26 at "major-minor nodes." In the current collector 10 of FIG. 1, the branch struts 42 depart from the radial struts 26 at an acute angle. The distal ends 46 of the branch struts 42 are connected to the undulating perimeter, preferably at the convexities 20 or the inflection nodes 24 thereof. Preferably, the distal ends of the branch struts 42 connect to the undulating structure of the sinusoidal frame at an angle greater than 90° from the connection of the distal end of another branch 42 or of a radial strut 26. The branch struts 42 may be linear or curvilinear.

Additionally, the junction 32 or node cluster 34 is located in the central region of the current collector. This is an advantageous configuration. Since certain cathode active materials expand outwardly after pressing to the current collector, locating the junction 32 or node cluster 34 closer to a relatively "movement neutral" or static zone of the pressed cathode active material is desirable. In other words, locating the junction 32 or node cluster 34 at or near the centroid of the conductive mesh 18 area embedded in the cathode active material helps minimize stress in the electrode assembly.

FIG. 1A is a detailed view of a terminal tab that is an alternative to the connection of the terminal tab 19 depicted in FIG. 1. Referring first to FIG. 1, the terminal tab 19 is connected to the frame conductor 16, to one radial strut 27, and to one branch strut 43. Referring to FIG. 1A, the terminal tab 21 is connected to the frame conductor 16, to radial strut 27, and to branch struts 43, 45 and 47. Connection may further be comprised of radiating terminal struts 49 which are joined to branch struts 43, 45 and 47. Connection of the terminal tab 21 to the current collector 10 is considered advantageous with respect to the capability to conduct current into or out of the current collector.

FIG. 1B is a detailed view of a sector of the current collector 10 of FIG. 1, showing compliance of the current collector. Sector 11 (shown in phantom, dash-double dot lines) is a portion of the current collector 10 in it's relatively stress free state, i.e. not subjected to any external forces. Sector 11E (shown in solid lines) is the same portion of the current collector 10 in an expanded state, which may result from subjecting the current collector 10 to stresses resulting from pressing of the cathode material to the collector, recoil after pressing, activating the electrode with electrolyte, and electrochemical reaction of the cathode active material during use of the cell. In that respect, the current collector 10 of the present invention undergoes strain, i.e. an expanding movement, to relieve those types of stresses. This stress relief minimizes warping of the electrode assembly and delamination of the electrode active material from the current collector 10. It is noted that the extent of the expansion of sector 11 to the approximate shape of sector 11E has been exaggerated for the sake of clarity of illustration.

FIG. 2 is a plan view of a second current collector 12 in accordance with the present invention. Current collector 12 is comprised of a frame 48 formed as a closed undulating perimeter, and a conductive mesh 50 formed within the frame 48. The current collector 12 may include a tab 52 extending from the frame conductor 48 for connection to a cell terminal (not shown). The undulating perimeter of the frame conductor 48 is comprised of a continuous sequence of convex regions 54, inflection nodes 56, and concave regions 58 as described previously for the current collector 10 of FIG. 1.

The conductive mesh 50 is comprised of a plurality of radial or major struts 60, each radial strut 60 having a central or proximal end 62 and an outer or distal end 64. The outer ends 64 of the radial struts 60 are connected to the undulating perimeter of the frame 48, preferably at the convexities 54 or at the inflection nodes 56. The radial struts 60 may be linear or curvilinear, emanating from a junction 66 located within and bounded by the undulating perimeter. In the current collector 12 of FIG. 2, the junction 66 is located near the undulating perimeter with the radial struts 60 extending outwardly thereto. The junction 66 may be contiguous with a portion of the frame 48 of the mesh. The radial struts 60 may be arrayed in an equally spaced radial pattern as shown in FIG. 2.

The conductive mesh 50 may further include the junction 66 being formed as a node cluster 68 comprised of a border 70 surrounding an opening 72. The central ends 62 of the radial struts 60 are connected to the node cluster 68. The portion of the border 70 of the node cluster 68 to which the radial struts 60 are connected may also undulate if the opening 72 is made sufficiently large, with the radial struts 60 preferably connected at the concavities (not shown) thereof. The conductive mesh 50 may be further comprised of branch or minor struts 76 having proximal ends 78 and distal ends 80, with the proximal ends 78 being connected to the major or radial struts 60 at major-minor nodes. The branch struts 76 may be linear or curvilinear. In general, the interconnections of the radial struts 60 and branch struts 76 of the mesh 50 form a leaf-like pattern of interconnected elements, with the branch struts 76 intersecting the radial struts 60 at an acute angle.

In the current collector 12 of FIG. 2, a branch strut 76 may be terminated in different ways, depending upon its particular location. Outer branch struts 82 extend from the outer radial struts 84 to the undulating perimeter of the frame conductor 48; Inner branch struts 86 are branch struts that traverse the portion of the mesh 50 between adjacent radial struts 60. In the current collector 12 of FIG. 2, the inner branch struts 86 depart from the radial struts 60 at an acute angle. Inner branch struts 86A that are more proximate to the junction 66 traverse between adjacent radial struts 60, departing a first radial strut at an acute angle α and intersecting an adjacent radial strut at an obtuse angle β. Inner branch struts 86B that are more proximate to the undulating perimeter of the frame conductor 48 traverse from a radial strut 60 to the undulating perimeter. These inner branch struts 86B preferably terminate at the convexities 54 or the inflection nodes 56 of the undulating perimeter. In one preferred embodiment, each of the convexities 88 (or a node adjacent thereto) located between a pair of adjacent radial struts 60 has a branch strut termination.

FIG. 3 is a plan view of a third current collector 14 in accordance with the present invention. Current collector 14 is comprised of a frame conductor 102 formed as a closed undulating perimeter, and a conductive mesh 104 formed within the frame 102. The current collector 14 may include a tab 106 extending from the frame 102 for connection to a cell terminal (not shown). The undulating perimeter of the frame 102 is comprised of a continuous sequence of convex regions 108, inflection nodes 110, and concave regions 112 as described previously for the current collector 10 of FIG. 1.

The conductive mesh 104 is comprised of a plurality of radial or major struts 114, each having a central or proximal end 116 and an outer or distal end 118. The outer ends 118 of the radial struts 114 are connected to the undulating perimeter of the frame 102, preferably at the convexities 108 or at the inflection nodes 110 thereof. The radial struts 114 may be linear or curvilinear, emanating from a junction 120 located within the undulating perimeter. In the current collector 14 of FIG. 3, the junction 120 is located near the undulating perimeter with the radial struts 114 extending outwardly to the undulating perimeter. The junction 120 may be contiguous with a portion of the frame conductor 104 of the mesh. The radial struts 114 may be arrayed in an equally spaced radial pattern as shown in FIG. 3. The Placement of the junction 120 near the frame conductor 102 of the current collector 14 is considered optimal for current flow through the current collector 104 and into the cathode active material (not shown). This is also the case for the current collector 12 of FIG. 2.

The conductive mesh 104 may further include the junction 120 being formed as a node cluster 122 comprised of a border 124 surrounding an opening 126. The central ends 116 of the radial struts 114 are connected to the node cluster 122. The portion of the border 124 of the node cluster 122 to which the radial struts 114 are connected may also undulate if the opening 126 is made sufficiently large, with the radial struts 114 preferably connected at the concavities (not shown) thereof. The conductive mesh 104 may be further comprised of branch or minor struts 130 having proximal ends 132 and distal ends 134, with the proximal ends 132 being connected to the major or radial struts 114 at major-minor nodes. In current collector 14, the proximal ends 132 of the branch struts are those ends located closest to the central branch strut 136. The branch struts 130 may be linear or curvilinear. In general, the interconnections of the radial struts 114 and branch struts 130 of the mesh 104 form a web-like pattern of interconnected elements, with the branch struts 130 intersecting the radial struts 114 at an approximately perpendicular angle.

Depending upon its particular location, a branch strut 130 of the current collector 14 shown in FIG. 3 may be terminated in different ways. Outer branch struts 138 extend from the outer radial struts 140 to the undulating perimeter of the frame conductor 102. The distal ends 142 of the outer branch struts 138 preferably connect to a inflection node 110 or a convexity 108 of the undulating perimeter. Inner branch struts 148 are struts that traverse the portion of the mesh 104 between adjacent radial struts 114. The inner branch struts 148A, which are those more proximate to the junction 120, traverse between adjacent radial struts 114. For these inner branch struts 148A, the two angles formed at the respective intersections with the adjacent radial struts 114 are approximately equal. Additionally, branch struts on opposite sides of a given radial strut 114 intersect the radial strut in a staggered pattern to reduce the number of strut connections at the major-minor nodes. The curvature pattern of the branch struts 130 may be reversed in direction from the junction 120 to the undulating perimeter, transitioning in the centroid region of the conductive mesh 104 from convex to concave. This reversal of curvature may also be provided in the radial struts 114 across the conductive mesh 104. Outer branch struts 148B, which are most proximate to the undulating perimeter of the frame 120, traverse from a radial strut 114 to the undulating perimeter.

The exemplary current collectors 10, 12 and 14 illustrated in respective FIGS. 1 to 3, all being comprised of a frame conductor formed as a closed undulating perimeter and a conductive mesh comprised of radial struts, differ from prior art screen current collectors having a regular pattern of openings such as circles, rectangles, squares, rhombi, etc. The use of such prior art current collectors has led to some difficulties in the manufacture of some cathode designs. A cathode comprising a screen or mesh current collector embedded within cathode active material is similar in some ways to other non-battery composite structures that employ physically reinforcing members such as wire cloth in concrete, or expanded metal lath in plaster. In such applications, the expanded metal lath or wire cloth acts to reinforce the composite structure by acting as a constraining element when the assembled structure is loaded in a tensile (i.e. pulling) mode. The uniform pattern of openings in the wire cloth or expanded metal enables encasement by the base material. The base components (plaster or concrete) typically have acceptable compressive strength for a given application, but relatively poor tensile strength, and therefore have a need for reinforcement. The base components maintain a substantially homogeneous constituency through and around the openings of the reinforcing elements; the reinforcing elements are 'cast' or 'frozen' in place when the base material is cured and solidified. During the curing process for the above non-cell structural examples, the base materials (plaster or concrete) may expand or contract at a rate different than that of the reinforcing elements, but typically not so significantly so as to become problematic. Thus, when cured, the resistance of the composite structure to any tensile movement will be accomplished by the porous reinforcing elements.

As noted previously herein, current collectors may provide structural reinforcement in cathodes. However, combinations of certain cathode materials formed in a composite matrix with current collectors of the prior art, which have a regular pattern of openings, have been problematic. In such cathodic structures, these prior art current collectors are not able to move sufficiently with the expansion of the cathodic base material during and/or after the manufacturing process. The resultant problem manifests itself via a physically constraining effect produced by the one or more embedded current collectors. Thus, stresses develop between the cathode active material and the current collector, and warping and/or delamination of the cathode often occurs.

In contrast, current collectors of the present invention, such as those of the exemplary embodiments illustrated as current collectors 10, 12, and 14 of FIGS. 1 to 3 avoid the problems of warping and delamination, and are therefore superior to prior art current collectors. Without wishing to be bound to any particular theory, it's believed that the combination of the frame conductor formed as a closed undulating perimeter and a conductive mesh comprised of radial struts provides stress relief in a cathode made with the instant current collectors. In particular, it's believed that the following benefits are obtained:

a) The use of elongated linear or curvilinear radial struts enables slippage and relocation of base electrode material (typically cathode active material) in directions along the radial struts, and deflection of the radial struts to move with the base material in directions essentially perpendicular to the radial struts. The optional curvature of the radial struts allows adjacent nodes to move apart, as imposed by the base material when it recoils after electrode pressing and when it expands after electrolyte addition and during cell use.

b) The reduction in the number of major-minor nodes between radial and branch struts (as compared to the large population of nodes in a finely divided regular pattern screen current collector) enables easier movement of the linear or curvilinear radial and branch struts with the base electrode material.

c) The undulating perimeter enables the general outward expansion of the base electrode material with reduced restriction. The curved portions are able to open and close as necessary to follow with the base material, i.e., the border is able to expand or contract as dictated by the base material. Delamination and excessive warping of the electrode are thus avoided.

d) The reversing of curvature of the branch struts in the direction from the junction to the undulating perimeter in the current collector 14 of FIG. 3 facilitates displacement of the current collector with the outward expansion of electrode base material. When the base material expands, as two adjacent major-minor nodes displace outwardly and apart from each other, the curvilinear branch strut between adjacent nodes is also displaced in a generally outward direction away from the centroid of the conductive mesh.

e) The junction 32 of the current collector 10 of FIG. 1 enables greater ease of movement of electrode base material. In other words, the more radial orientation of linear or curvilinear elements enables an easier "following" of the linear or curvilinear elements of the current collector with the base material.

The exemplary current collectors 10, 12, and 14 of FIGS. 1 to 3 are preferably made of a conductive metal such as aluminum, stainless steel, or titanium, but may be made of any electrically conductive material. The current collectors 10, 12 and 14 may be used for cathodic and anodic structures, and may include additional features to further optimize their performance. The radial struts and the branch struts of the current collectors may incorporate a taper along their respective lengths. The struts would be thinnest at distances furthest away from the junction or node cluster. The tapering may be in the width and in the thickness of the struts. The branch struts may have a lesser width than the radial struts.

Figure 4:
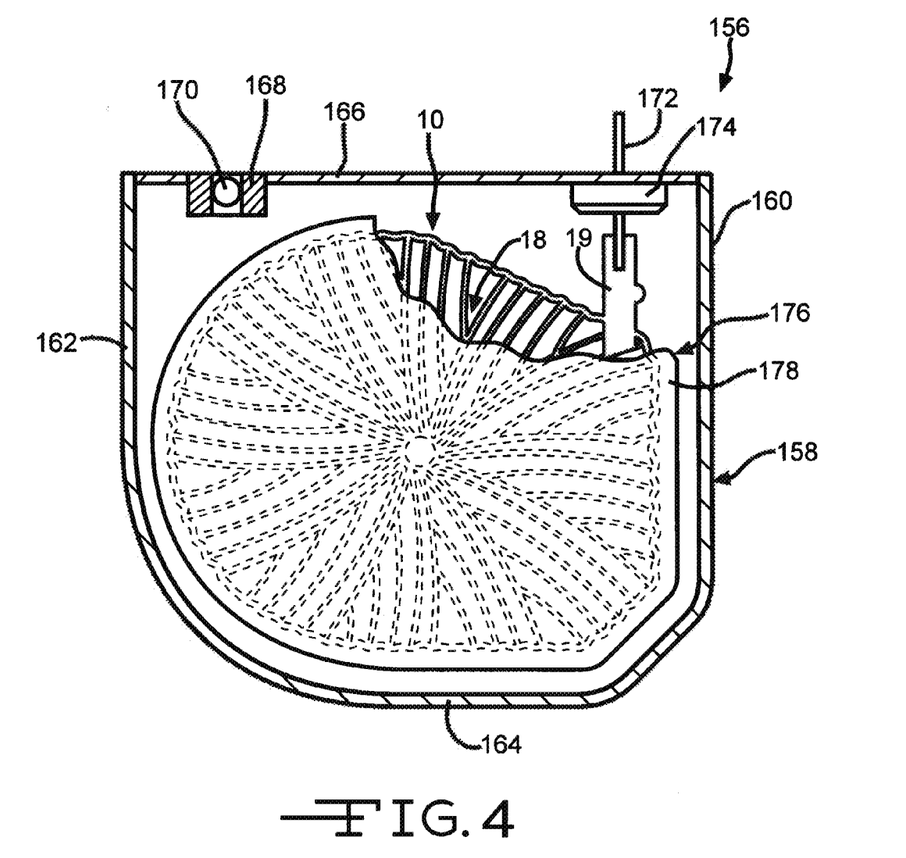
FIG. 4 is a partial cutaway view of an electrochemical cell 156 including the current collector 10 of FIG. 1.

The above current collectors may be used in electrochemical cells. FIG. 4 is a partial cutaway view of an electrochemical cell 156 including the current collector 10 of FIG. 1. Either of the current collectors 12 or 14 of FIGS. 2 and 3 may be substituted for the current collector 10 in cell 156.

The cell 156 includes a casing 158 having spaced apart front and back side walls (not shown) joined by sidewalls 160 and 162 and a bottom wall 164. A lid 166 closes the open top of the casing 158. Lid 166 has an opening 168 that serves as a port for filling an electrolyte (not shown) into the casing after the cell's internal components have been assembled therein and lid 166 has been sealed to the side walls. In the final and fully assembled condition, a plug, such as a ball 170, is hermetically sealed in the electrolyte fill opening 168 to close the cell in a gas tight manner. The casing 158, lid 166 and sealing ball 170 are preferably of a conductive material. Suitable materials include nickel, aluminum, stainless steel, mild steel, nickel-plated mild steel and titanium. Preferably, the casing, lid and sealing ball are of the same material.

A terminal lead 172 for one of the anode and the cathode is electrically insulated from the lid 166 and the casing 158 by a glass-to-metal seal 174. In a case-negative cell configuration, the lead 172 serves as the cathode terminal and the lid 166 and casing 158 serve as the negative or anode terminal, as is well known to those skilled in the art. A case-positive cell configuration has the positive electrode or cathode contacted to the casing 158 with the anode supported on the current collector 10 connected to the lead 172.

In either case, the exemplary cell 156 shown in FIG. 4 includes a central electrode 176 comprising the current collector 10 of the present invention supporting at least one of the opposite polarity active materials. For the sake of clarity, the active materials are not shown supported on the current collector 10. However, in a case-negative cell configuration, current collector 10 supports opposed layers of cathode active material contacting the opposite major sides thereof locked together through its many openings in the conductive mesh 18. The tab 19 is then connected to the terminal lead 172 such as by welding. In a case-positive cell configuration, anode active material is locked together supported on the opposite major sides of the current collector 10. The central electrode 176 of cell 156 is sealed in a separator envelope 178 to prevent direct contact with the opposite polarity electrodes.

The cell 156 can be of either a primary or a secondary chemistry. A preferred primary electrochemical cell is of an alkali metal anode, such as of lithium, and a solid cathode active material. Exemplary cathode materials include silver vanadium oxide (SVO), copper silver vanadium oxide, manganese dioxide and fluorinated carbon ($CF_x$). An exemplary secondary cell has a carbonaceous anode and a lithiated cathode active material such as lithium cobalt oxide. In either type of cell chemistry, the activating electrolyte is typically of a nonaqueous nature.

EXAMPLES

Sets of current collectors according to the present invention were prepared by chemical etching of titanium sheet having a thickness of about 0.002 inches. A set of "control" current collectors were also made. The control current collectors were from an existing product and thus had a known performance history. The screen pattern of the control current collectors was comprised of a regularly repeating pattern of rhombi having sides of about 0.026 inch, an acute angle of about 60 degrees, and a strand width of about 0.009 inch, which produced an open area of about 50 percent.

Sets of thirty cathode assemblies were fabricated, each set containing one of the current collectors 10, 12 and 14 of the present invention. A set of eighteen cathode assemblies was also prepared containing the control current collectors. Each cathode assembly was comprised of two current collector screens contacted with $CF_x$ and SVO in the configuration SVO/screen/$CF_x$/screen/SVO. Within each group, half of the cathode assemblies had the $CF_x$ pressed at 8 kpsi (thousand pounds per square inch) and half had the $CF_x$ pressed at 14 kpsi.

Cupping measurements were made for each cathode assembly. The term "cupping" refers to the extent to which the finished cathode becomes concave on one side and convex on the other. To determine the cupping of an electrode assembly, a mid-thickness measurement is taken with the concave side down. The assembly is then inverted and another mid-thickness measurement is taken. The difference between the two values is the cupping difference for that assembly. Cupping is an important parameter because it provides a cathode assembly with a greater apparent thickness than its actual thickness measured from an upper to a lower surface. Thus, during cell fabrication, excessive cupping can make it difficult for an operator to insert a cathode assembly into the cell case.

Cupping was observed to some extent on all cathode assemblies. The control group screens displayed the most cupping. On average, the cupping of control screens was greater than 0.0100" for cathode assemblies made with the low pressure $CF_x$ blanks (8 kpsi). Control assemblies made with the high pressure $CF_x$ blanks (14 kpsi) typically showed cupping greater than 0.0170". Assemblies made using current collector screens of the present invention displayed cupping on average under 0.0050". Average cupping data for the various screen types is presented in Table 1.

TABLE 1

| SCREEN TYPE | SAMPLE SIZE | $CF_x$ PRESSING PRESSURE (kpsi) | AVERAGE CUPPING (IN.) |
|---|---|---|---|
| CONTROL: | 12 | 8 | 0.0128 |
| 0.026" × 60° RHOMBI | 12 | 14 | 0.0177 |
| "SPOKE" TYPE | 15 | 8 | 0.0005 |
| (FIG. 1) | 15 | 14 | 0.0003 |
| "LEAF" TYPE | 15 | 8 | 0.0028 |
| (FIG. 2) | 15 | 14 | 0.0019 |
| "WEB" TYPE | 15 | 8 | 0.0010 |
| (FIG. 3) | 15 | 14 | 0.0014 |

It can be seen that the extent of cupping in all of the current collectors of the present invention is significantly less than that of the control samples. The data indicate that the current collectors of the present invention serve to relieve stress that may arise in the cathode assemblies. They deform compliantly with the cathode base material during and immediately following contact and pressing of the cathode material to the collector, after the cathode is activated with electrolyte, and during use of the cell as the cathode active material undergoes the electrochemical reactions.

It is, therefore, apparent that there has been provided, in accordance with the present invention, a compliant current collector for an electrochemical cell. While this invention has been described in conjunction with preferred embodiments thereof, it is evident that many alternatives, modifications, and variations will be apparent to those skilled in the art. Accordingly, the present invention is intended to embrace all such alternatives, modifications and variations that fall within the broad scope of the appended claims.

What is claimed is:

1. A current collector, comprising:
   a) a frame conductor having a closed perimeter comprising a repeating sequence of a concave undulation extending to and meeting with a convex undulation;
   b) a node at either an interior location inside the frame conductor or connected to the frame conductor; and
   c) at least a first radial strut and a second radial strut, both the first and second radial struts comprising a proximal radial strut end connected to the node and a distal radial strut end connected to the frame conductor,
   d) wherein the closed perimeter is expandable such that in an unexpanded state, the distal ends of the first and second radial struts are spaced apart by a first distance and in an expanded state, the distal ends of the first and second radial struts are spaced apart by a second distance that is greater than the first distance.

2. The current collector of claim 1 wherein the closed perimeter comprising the sequence of the concave undulation extending to the convex undulation has a generally sinusoidal shape.

3. The current collector of claim 1 wherein the node is comprised of a nodal border surrounding an opening, and wherein the proximal radial strut end of the at least one radial strut is connected to the nodal border.

4. The current collector of claim 1 wherein the node is at the interior location inside the frame conductor, but not connected to the frame conductor.

5. The current collector of claim 1 further comprised of at least one branch strut having a proximal branch strut end connected to the at least one radial strut and a distal branch strut end connected to the frame conductor.

6. The current collector of claim 5 wherein there are a plurality of branch struts, each having a distal branch strut end connected to the frame conductor.

7. The current collector of claim 1 wherein with the node being a focal point, a first radial strut is connected to the frame conductor at least 90° away from where a second radial strut is connected to the frame conductor.

8. The current collector of claim 1 wherein the node is contiguous with a portion of the frame conductor.

9. The current collector of claim 5 wherein there is a plurality of branch struts, each having a proximal branch strut end connected to a radial strut.

10. The current collector of claim 1 further comprised of at least one branch strut having a proximal branch strut end connected to a first radial strut and a distal branch strut end connected to an adjacent second radial strut.

11. The current collector of claim 1 further comprising a tab extending from the frame conductor at the node.

12. The current collector of claim 1 wherein the at least one radial strut emanates from a junction location of the node connected to the frame conductor.

13. The current collector of claim 1 wherein the at least one radial strut emanates from a junction location of the node and a tab connected to the frame conductor.

14. The current collector of claim 1 wherein the at least one radial strut is connected to the frame conductor at a convex undulation.

15. The current collector of claim 1 wherein the at least one radial strut is connected to the frame conductor at an inwardly projecting apex of a convex undulation.

16. The current collector of claim 1 wherein the at least one radial strut is linear.

17. The current collector of claim 1 wherein the at least one radial strut is curvilinear.

18. The current collector of claim 1 further comprised of at least one branch strut having a proximal branch strut end connected to the at least one radial strut and a distal branch strut end connected to a convex undulation of the frame conductor.

19. The current collector of claim 18 wherein the distal branch strut end is connected to an inwardly projecting apex of the convex undulation of the frame conductor.

20. The current collector of claim 1 further comprised of at least one branch strut having a proximal branch strut end connected to the at least one radial strut and a distal branch strut end connected to a concave undulation of the frame conductor.

21. The current collector of claim 20 wherein the distal branch strut end is connected to an outwardly projecting trough of the convex undulation of the frame conductor.

22. The current collector of claim 10 wherein the at least one branch strut is linear.

23. The current collector of claim 10 wherein the at least one branch strut is curvilinear.

24. An electrochemical cell, comprising:
   a) a current collector comprised of:
      i) a frame conductor having a closed perimeter comprising a repeating sequence of a concave undulation extending to and meeting with a convex undulation;
      ii) a node at either an interior location inside the frame conductor or connected to the frame conductor; and
      iii) at least a first radial strut and a second radial strut, both the first and second radial struts comprising a proximal radial strut end connected to the node and a distal radial strut end connected to the frame conductor,
      iv) wherein the closed perimeter is expandable such that in an unexpanded state, the distal ends of the first and second radial struts are spaced apart by a first distance and in an expanded state, the distal ends of the first and second radial struts are spaced apart by a second distance that is greater than the first distance; and
   b) a first electrode active material contacted to at least one of a first and second major sides of the current collector having its frame conductor connected to a first terminal to provide a first electrode;
   c) a second, counter electrode connected to a second terminal and electrochemically associated with the first electrode to thereby form an electrode assembly; and
   d) an electrolyte activating the electrode assembly housed inside a casing.

25. A method for providing an electrochemical cell, comprising the steps of
   a) providing a current collector comprising:
      i) a frame conductor having a closed perimeter comprising a repeating sequence of a concave undulation extending to and meeting with a convex undulation;
      ii) a node at either an interior location inside the frame conductor or connected to the frame conductor; and
      iii) at least a first radial strut and a second radial strut, both the first and second radial struts comprising a proximal radial strut end connected to the node and a distal radial strut end connected to the frame conductor, iv) wherein the closed perimeter is expandable such that in an unexpanded state, the distal ends of the first and second radial struts are spaced apart by a first distance and in an expanded state, the distal ends of the first and second radial struts are spaced apart by a second distance that is greater than the first distance; and b) contacting a first electrode active material to at least one of a first and a second major sides of the current collector;

electrically connecting the frame conductor of the current collector supporting the first electrode active material to a first terminal to provide a first electrode;

d) electrochemically associating the first electrode with a second, counter electrode connected to a second terminal to thereby provide an electrode assembly; and e) activating the electrode assembly housed inside a casing with an electrolyte.

26. The electrochemical cell of claim 24 wherein a separator is disposed between the first and second electrodes to prevent direct physical contact between them.

27. The method of claim 25 including providing a separator between the first and second electrodes to prevent direct physical contact between them.

28. The current collector of claim 1 having a thickness between an upper current collector surface and a lower current collector surface, wherein in both the unexpanded and the expanded states the current collector exhibits a deflection from an imaginary plane bisecting the thickness mid-way between the upper and lower current collector surfaces that is not greater than about 0.0028 inches.

29. The current collector of claim 24 having a thickness between an upper current collector surface and a lower current collector surface, wherein in both the unexpanded and the expanded states the current collector exhibits a deflection from an imaginary plane bisecting the thickness mid-way between the upper and lower current collector surfaces that is not greater than about 0.0028 inches.

30. The method of claim 25 including the current collector having a thickness between an upper current collector surface and a lower current collector surface, wherein in both the unexpanded and the expanded states the current collector exhibits a deflection from an imaginary plane bisecting the thickness mid-way between the upper and lower current collector surfaces that is not greater than about 0.0028 inches.

\* \* \* \* \*

UNITED STATES PATENT AND TRADEMARK OFFICE
CERTIFICATE OF CORRECTION

| | | |
|---|---|---|
| PATENT NO. | : 8,741,487 B1 | Page 1 of 1 |
| APPLICATION NO. | : 12/549435 | |
| DATED | : June 3, 2014 | |
| INVENTOR(S) | : Duggan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 994 days.

In the Claims:

Column 13, line 13 (Claim 25, line 23) before the word "electrically" insert --c)--

Signed and Sealed this
Twenty-second Day of December, 2015

Michelle K. Lee
*Director of the United States Patent and Trademark Office*